US007118377B2

(12) United States Patent
Inoue et al.

(10) Patent No.: US 7,118,377 B2
(45) Date of Patent: Oct. 10, 2006

(54) DENTAL SYSTEM AND METHOD OF PRODUCING THE SAME

(76) Inventors: Yoshinori Inoue, Nojima Park Sofare 102, 16-5, Otsutomo-cho, Kanazawa-ku, Yokohama-shi, Kanagawa (JP); Hisaaki Shinji, 2-38-11, Maborikaigan, Yokosuka-shi, Kanagawa (JP); Noboru Uchimura, 2-11-36, Nagata-higashi, Minami-ku, Yokohama-shi, Kanagawa (JP)

( * ) Notice: Subject to any disclaimer, the term of this patent is extended or adjusted under 35 U.S.C. 154(b) by 241 days.

(21) Appl. No.: 10/766,002

(22) Filed: Jan. 29, 2004

(65) Prior Publication Data

US 2005/0037315 A1     Feb. 17, 2005

(30) Foreign Application Priority Data

Aug. 13, 2003   (JP) ............................. 2003-292753

(51) Int. Cl.
*A61C 17/00* (2006.01)
(52) U.S. Cl. ............................. 433/80; 433/86; 433/93
(58) Field of Classification Search .................. 433/80, 433/86, 91, 93, 216
See application file for complete search history.

(56) References Cited

U.S. PATENT DOCUMENTS

| | | | | | |
|---|---|---|---|---|---|
| 803,474 | A | * | 10/1905 | Dennis | 433/80 |
| 3,380,446 | A | * | 4/1968 | Martin | 601/2 |
| 3,401,690 | A | * | 9/1968 | Martin | 604/22 |
| 3,527,218 | A | * | 9/1970 | Westine | 433/80 |
| 3,566,869 | A | | 3/1971 | Crowson | |
| 3,731,675 | A | * | 5/1973 | Kelly | 601/164 |
| 4,106,501 | A | * | 8/1978 | Ozbey et al. | 601/164 |
| 4,164,940 | A | * | 8/1979 | Quinby | 601/164 |
| 4,560,351 | A | * | 12/1985 | Osborne | 433/80 |
| 5,104,315 | A | * | 4/1992 | McKinley | 433/80 |
| 5,443,386 | A | | 8/1995 | Viskup | |
| 5,460,527 | A | | 10/1995 | Kittelsen | |
| 6,893,259 | B1 | * | 5/2005 | Reizenson | 433/29 |

FOREIGN PATENT DOCUMENTS

| | | |
|---|---|---|
| JP | 63-82656 | 4/1988 |
| JP | U 6-64522 | 9/1994 |
| JP | 2001-340412 | 12/2001 |
| JP | A 2002-45378 | 2/2002 |

OTHER PUBLICATIONS

Takeuchi, Hiroaki et al. "New Dental Drug Delivery System for Removing Mutans Streptococci from the Oral Cavity: Effect on Oral Microbial Flora." *Laboratory and Epidemiology Communications* Japan Journal of Infectious Diseases 53, 2000.

* cited by examiner

*Primary Examiner*—Ralph A. Lewis
(74) *Attorney, Agent, or Firm*—Oliff & Berridge, PLC

(57) ABSTRACT

A dental system for cleaning a user's teeth and marginal gingiva with a drug solution includes a mouthpiece made for each user and having substantially the same shape as the teeth and the marginal gingiva of the user. The mouthpiece is designed to produce a gap between the mouthpiece and the teeth together with the marginal gingiva when placed to cover the teeth and the marginal gingiva of the user. The dental system also includes a drug solution supply unit and a drain unit, both connected to the mouthpiece, and a suction unit connected to the drain unit. The mouthpiece adheres to the marginal gingiva by a suction applied from the suction unit. The dental system cleans the teeth and the marginal gingiva with a stream of the drug solution flowing through the gap.

14 Claims, 7 Drawing Sheets

DENTAL SYSTEM AND METHOD OF PRODUCING THE SAME

BACKGROUND OF THE INVENTION

1. Field of the Invention

The present invention relates to a dental system for cleaning and disinfecting teeth and marginal gingiva, and a method of producing the same.

2. Related Background Art

Conventional methods of cleaning and disinfecting teeth and marginal gingiva involve brushing teeth and gingiva using a toothbrush with dentifrice having cleaning and sterilizing effects. Recently, electric toothbrushes have been developed that apply vibration to teeth and gingiva for cleaning and gingival massage. Use of the electric toothbrush only requires holding the electric toothbrush with one hand and shifting it to change the position of bristle tips against the teeth, causing less hand fatigue than manual toothbrushing.

The use of the electric toothbrush, however, can undesirably stimulate the vomiting reflex when brushing the tong side (backside) of teeth. This causes users to have an aversion to toothbrushing or fail in proper toothbrushing, which could lead to dental caries, gingivitis, or alveolar pyorrhea. Besides, when using the electric toothbrush for those who are bedridden or have handicap with hand, it is difficult to place the bristle tips of the brush in a suitable position and brush every tooth.

Further, when a caregiver brushes the teeth of a carereceiver, placing a toothbrush against a target back tooth is difficult. It is thus likely to push the brush against the marginal gingiva so hard that it bleeds. Furthermore, the bristle tips of the brush are hard to reach the tong side (backside) of teeth because of a tong being obstacle. Food debris is thus likely to be deposited on the teeth, causing dental caries, gingivitis, or alveolar pyorrhea.

As a solution to the above problems, alternative toothbrushing techniques without the use of the electric toothbrush have been proposed. Among those is a technique that squirts a stream of water or disinfectant out of a nozzle into a mouth, thereby cleaning teeth and marginal gingiva. This technique of shooting water or a drug solution such as gargle at teeth and marginal gingiva, however, forces users to bear the unpleasant flavor of the drug solution. Further, the drug solution may leak from the mouth or enter into the airway, inducing misswallowing.

Another technique uses a mouthpiece made to fit on the teeth. This technique applies a drug agent to the inner surface of a mouthpiece and places the mouthpiece in an oral cavity to disinfect teeth and marginal gingiva. This technique, however, has a disinfection effect only and not removes deposits on the teeth and marginal gingiva; consequently, it only achieves a reduced sterilizing effect. Further, the drug solution leaking out of the mouthpiece touches a tongue, forcing users to bear an unpleasant flavor. In addition, when detaching the mouthpiece, considerable drug solution touches the tongue to bring an unpleasant flavor.

An example of oral cavity cleaning instruments for the cleaning of oral cavity, especially teeth and marginal gingiva, is disclosed in Japanese UtilityModel Application Laid-Open No. H06-64522. It describes a dental and oral cleaning system that cleans teeth with a cleaning solution flowing in a mouthpiece. This system leaves gaps between the mouthpiece and marginal gingiva, and hence the cleaning solution leaks into the oral cavity, forcing users to bear an unpleasant flavor. Another example is a mouthpiece-shaped oral cavity cleaning appliance disclosed in Japanese Patent Application Laid-Open No. 2002-45378. It also has the problem that a drug solution leaks into an oral cavity during cleaning, causing users discomfort.

As described in the foregoing, conventional cleaning instruments fail to offer comfortable cleaning of teeth and marginal gingiva since a drug solution contacts the entire mucosa of an oral cavity.

SUMMARY OF THE INVENTION

The present invention has been accomplished to solve the above problems and an object of this invention is thus to provide a dental system that can offer comfortable cleaning of teeth and marginal gingiva, and a production method thereof.

A dental system according to the present invention for cleaning a user's teeth and marginal gingiva with a drug solution includes a mouthpiece made for each user, having substantially the same shape as the teeth and the marginal gingiva of the user, for covering the teeth and the marginal gingiva of the user while creating a gap between the mouthpiece and the teeth together with the marginal gingiva; a supply unit (a supply tank 12 in an embodiment of the invention, for example) connected to the mouthpiece, for supplying the drug solution to the mouthpiece; a drain unit (a drain tank 13 in an embodiment of the invention, for example) connected to the mouthpiece, for collecting the drug solution supplied to the mouthpiece by the supply unit; and a suction unit (a suction unit 15 in an embodiment of the invention, for example) connected to the drain unit, for introducing the drug solution from the supply unit into the mouthpiece by applying suction to the drain unit. In the dental system, the mouthpiece adheres to the marginal gingiva by the suction, and a stream of the drug solution flowing through the gap cleans the teeth and the marginal gingiva. This structure allows comfortable cleaning of teeth and marginal gingiva.

The mouthpiece does not necessarily cover the entire teeth and marginal gingiva of the user; it may cover only a part of them.

Preferably, the supply unit has a tube branching into at least two tubes, one tube for supplying the drug solution through a vicinity of a right back tooth of the user wearing the mouthpiece, another tube for supplying the drug solution through a vicinity of a left back tooth of the user. This ensures cleaning of teeth and marginal gingiva from back to front.

Further, the mouthpiece preferably comprises a flexible resin for touching a jaw of the user wearing the mouthpiece, and a rigid resin adhering to the flexible resin. This allows a user to wear the mouthpiece without discomfort.

It is also preferred that the supply unit is connected to a back tooth portion of the mouthpiece to supply the drug solution through the back tooth portion, and the drain unit is connected to a front tooth portion of the mouthpiece to supply the drug solution through the front tooth portion. This allows effective cleaning of teeth and marginal gingiva from back to front.

Furthermore, the supply unit preferably supplies the drug solution via a route from the front tooth portion, through an inside of the mouthpiece, to the back tooth portion. This prevents the supply unit from interfering with cleaning.

The dental system may include a vibrating unit (a vibrating unit 18 in an embodiment of the invention, for example)

connected to the mouthpiece, for applying vibration to the mouthpiece. This enables cleaning of every tooth and marginal gingiva.

Desirably, the vibrating unit is connected to a front tooth portion of the mouthpiece to apply vibration to the mouthpiece through the front tooth portion. This prevents the vibrating unit from interfering with cleaning.

A method of producing a dental system according to the present invention for cleaning a user's teeth and marginal gingiva with a drug solution includes steps of making a dental mold having substantially the same shape as the teeth and the marginal gingiva of the user; attaching a first resin onto the dental mold; attaching a second resin onto the first resin; stripping the first resin and the second resin out of the dental mold, and creating a first hole and a second hole penetrating the first resin and the second resin; stripping a part of the first resin placed on a tooth portion and a vicinity of the tooth portion the dental mold out of the second resin; connecting a supply unit (a supply tank 12 in an embodiment of the invention, for example) to the first hole, for supplying the drug solution; connecting a drain unit (a drain tank 13 in an embodiment of the invention, for example) to the second hole, for collecting the drug solution; and connecting a suction unit (a suction unit 15 in an embodiment of the invention, for example) to the drain unit, for sucking up the drug solution from the supply unit through the drain unit. This structure allows comfortable cleaning of teeth and marginal gingiva.

The method of producing a dental system according to the invention may further comprise a step of creating a third hole penetrating the first resin and the second resin; and a step of connecting a vibrating unit (a vibrating unit 18 in an embodiment of the invention, for example) to the third hole, for applying vibration. This enables cleaning of every tooth and marginal gingiva.

The method of producing a dental system according to the invention may further comprise a step of attaching a third resin onto a part of the second resin where the supply unit is placed, to cover the part with the third resin. This prevents the supply unit from interfering with cleaning.

Preferably, the step of stripping the first resin out of the second resin comes after the step of attaching the third resin. This allows effective creation of a flow path for a drug solution to flow through the dental system.

The present invention can thereby provide a dental system that enable to offer comfortable cleaning of teeth and marginal gingiva, and a production method of the dental system.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE PREFERRED EMBODIMENTS

A preferred embodiment of a dental system in accordance with the present invention is explained hereinafter in detail with reference to the drawings.

The dental system may be used as a dental cleaner with a mouthpiece for cleaning teeth and marginal gingiva or a gingival massager for massaging marginal gingiva. The dental system may be also used as a tooth surface cleaner with a mouthpiece for whitening teeth or a dental care appliance with a mouthpiece for treating dental caries, gingivitis, alveolar pyorrhea, and so on. A set of dental systems are needed for one user: one for the upper teeth and the other for the lower one. The systems may be used separately or simultaneously.

Figure 1:
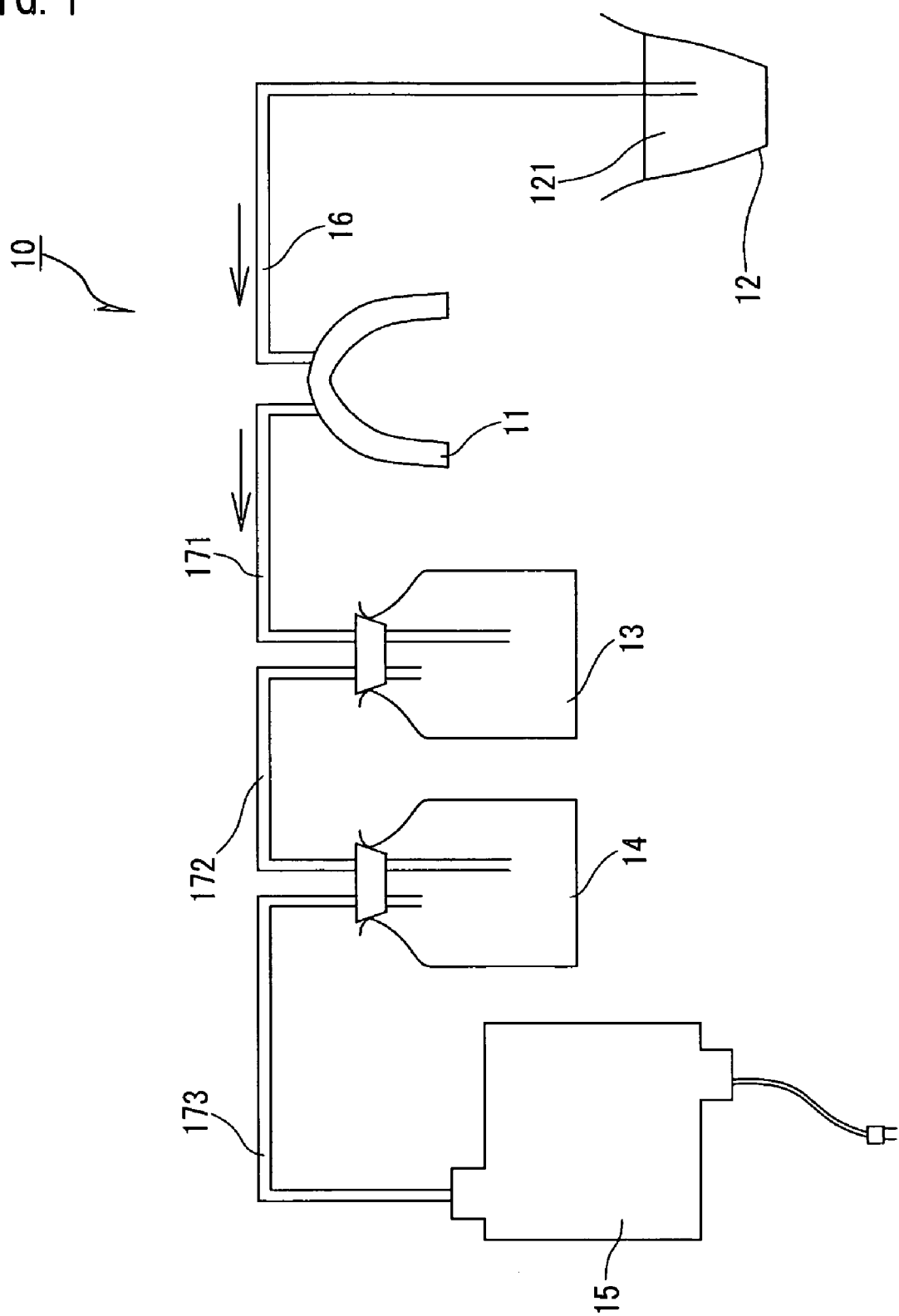
FIG. 1 is a block diagram showing a dental system in accordance with one embodiment of the invention.

The entire structure of the dental system according to this invention is explained first with reference to FIG. 1. FIG. 1 is a schematic block diagram showing an exemplary structure of the dental system according to the invention.

Referring to FIG. 1, a dental system 10 includes a mouthpiece 11, a drug solution supply tank 12, a drain tank 13, a buffer tank 14, a suction unit 15, a supply tube 16, a drain tube 171, a transfer tube 172, and a suction tube 173.

The mouthpiece 11 is a mouthpiece for oral cavity cleaning, used to bring a drug solution 12 into contact with teeth and marginal gingiva. The mouthpiece 11 has a unique shape for each user as described later. The mouthpiece 11 fits over an upper or lower dental arch and marginal gingiva during use of the dental system 10.

The drug solution supply tank 12 contains the drug solution 121. For cleaning of teeth and marginal gingiva, the drug solution 121 may be water, Oxiful (a hydrogen peroxide solution available from Sankyo, Co., Ltd., Tokyo, Japan), a commercially available mouthwash, or other cleaning solutions. For sterilization of teeth and marginal gingiva, the drug solution 121 may be Isodine (a povidine iodine solution available from Meiji Seika KK, Tokyo, Japan), a chlorhexidine solution, a triclosan solution, Listerin (Pfizer Inc., New York, USA), acid electrolyzed water, alkaline electrolyzed water, or other antiseptic solutions or antibacterial agents. Further, the drug solution 121 may be a medicinal agent beneficial to teeth and gingiva such as 2% sodium fluoride or stannous fluoride solution for strengthening teeth, or amphotericin B or fluconazole solution for disinfecting gingiva.

The drain tank 13 contains the drug solution 121 that has been used for cleaning. The buffer tank 14 is provided to safeguard against inflow of the drug solution 121 in the drain tank 13 into the suction unit 15, which is electric equipment. The suction unit 15 is a unit for air suction such as a suction pump.

The supply tube 16 connects between the mouthpiece 11 and the drug solution supply tank 12. The drain tube 171 connects between the mouthpiece 11 and the drain tank 13. The drain tube 171 has a larger diameter than the supply tube 16 to enable suction of the drug solution 121 from the supply tube 16. The transfer tube 172 connects between the drain tank 13 and the buffer tank 14. The suction tube 173 connects between the buffer tank 14 and the suction unit 15.

Thus, in the dental system 10, the mouthpiece 11 is connected to the drug solution supply tank 12 by the supply tube 16, and also to a train of the drain tank 13, buffer tank 14, and suction unit 15 connected by the drain tube 171, transfer tube 172, and suction tube 173, respectively. Though the dental system 10 in this embodiment has the buffer tank 14 between the drain tank 13 and the suction unit 15, the buffer tank 14 is not required if there is no inflow of the drug solution 121 into the suction unit 15.

A structure of the mouthpiece 11 in the dental system 10 is now explained in detail with reference to FIGS. 2 to 4. Though the explanation is given on the mouthpiece 11 for upper teeth, the structure is the same for a mouthpiece for lower teeth.

Figure 2A:
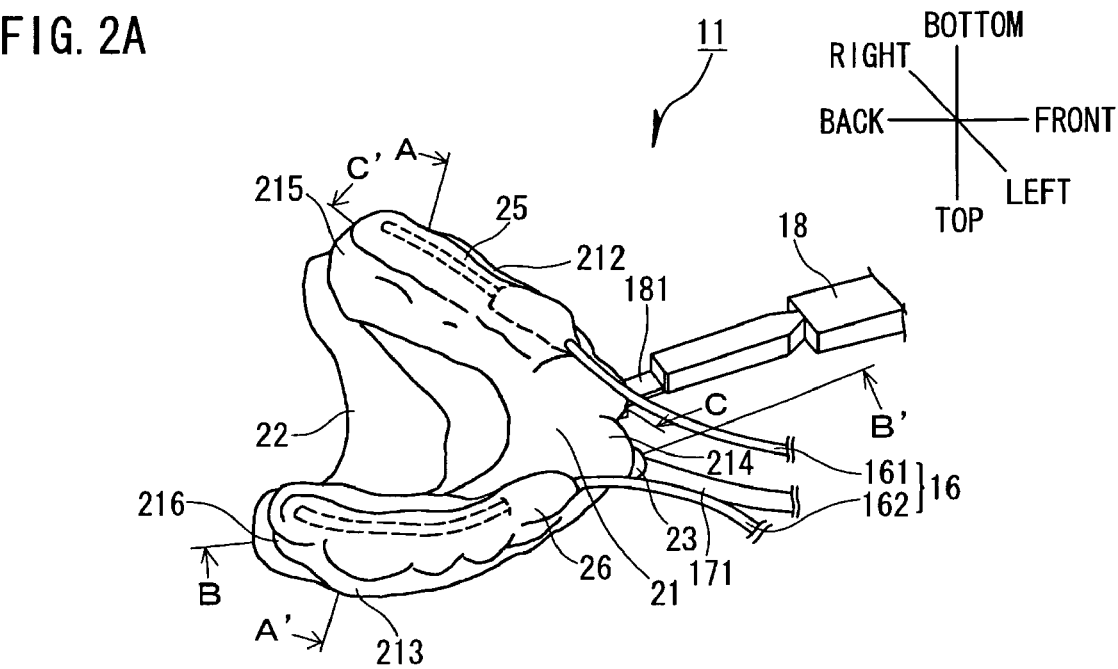
FIGS. 2A and 2B are perspective views showing a mouthpiece in accordance with one embodiment of the invention.

FIG. 2A is a perspective view showing the obverse side of the mouthpiece 11, and 2B the reverse side. The top and bottom, front and back, and left and right of the mouthpiece 11 corresponds to those of a user wearing the mouthpiece 11 on the upper teeth, and the obverse side refers to the side facing toward the lower jaw, and the reverse side toward the upper jaw.

Referring to FIG. 2A, the mouthpiece 11 comprises a vibrating unit 18 in addition to the supply tube 16 and the drain tube 171. The supply tube 16 consists of a set of supply tubes 161 and 162.

The vibrating unit 18 makes a tip portion 181 vibrate with electric power coming from a power source such as an internal buttery. It may be a shaft of a commercially available electric toothbrush whose brush portion is removed from its tip. Though the vibrating unit 18 applies vibration to the mouthpiece 11 by direct connection in this example, the vibration may be applied thereto by wireless connection. This saves users from holding the vibrating unit 18, allowing more comfortable tooth and gingival cleaning and gingival massage.

Figure 2B:
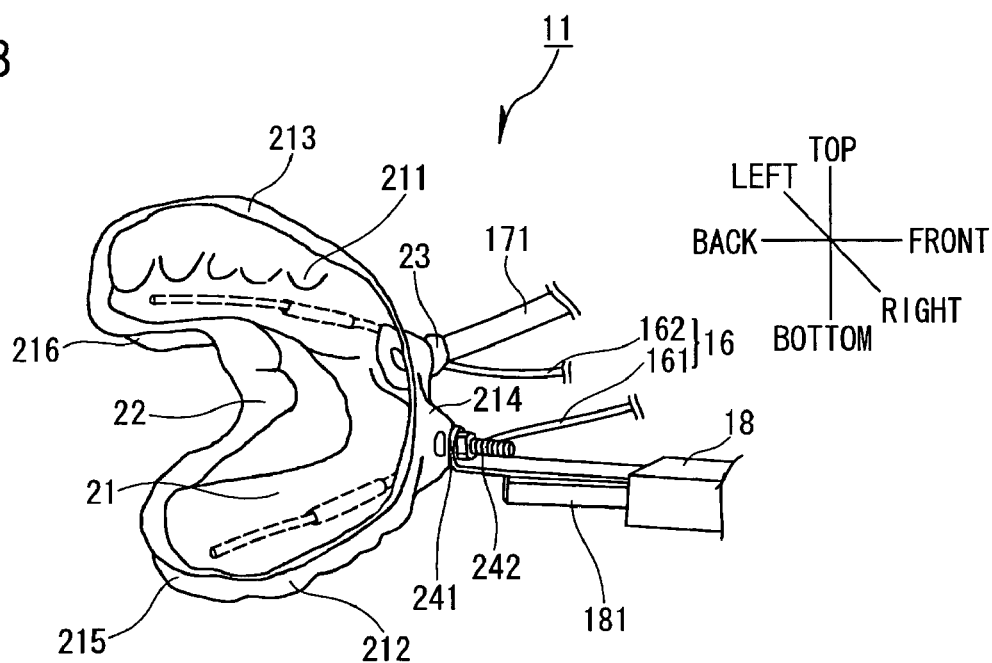

Referring now to FIG. 2B, the mouthpiece 11 is made up of a dentition covering part 21 and an upper jaw covering part 22.

The dentition covering part 21, made of flexible resin, has an elongated curved U-shape to follow the shape of an upper dental arch. The dentition covering part 21 is designed to have hollow portions 211. The hollow portions are substantially U-shaped, provided side by side along the elongated dentition covering part 21. Specifically, the dentition covering part 21 has substantially the same shape as an upper dental arch and marginal gingiva to fit almost perfectly over them.

The upper jaw covering part 22, on the other hand, has an elliptical shape in which the U-shape is removed, also made of elastic material. The upper jaw covering part 22 is attached to the dentition covering part 21 along its curved edge, providing a smooth continuous connection between an inner right side portion 22 and an inner left side portion 23. The inner side of the dentition covering part 21 refers to the recessed side of the U-shape, which is, the side without the vibrating unit 18 in FIGS. 2A and 2B. The outer side refers to the side different from the inner side.

The drain tube 171 and the vibrating unit 18 are connected to a front portion 214 of the dentition covering part 21. The front portion 214 is between the right side portion 212 and the left side portion 213, near the center of the U-shape of the dentition covering part 21. The dentition covering part 21 has penetration holes (not shown in FIG. 2) for the drain tube 171 and the vibrating unit 18. The drain tube 171 and the vibrating unit 18 are attached to the dentition covering part 21 by inserted into the holes. The attachment uses adhesives 23 and 241 made of a synthetic resin such as a self-curing resin. Attachment portions are hermetically sealed up to prevent the fluid inside the dentition covering part 241 from leaking through the holes during use of the mouthpiece 11. The vibrating unit 18 is fixed with a screw 242 before secured with the adhesive 241. For easier connection of the drain tube 171 and of the vibrating unit 18, the front portion 214 has a domed shape.

As shown in FIG. 2A, the dentition covering part 21 has bumps 25 and 26 along the right side portion 212 and the left side portion 213, respectively. One ends of the supply tubes 161 and 162 are buried in the bumps 25 and 26, respectively, so that the drug solution 121 is supplied inside the mouthpiece 11 through the inside of the bumps. The supply tubes 161 and 162 supply the drug solution 121 into the dentition covering part 21 from the right end 215 and the left end 216 of the dentition covering part 21. The right end 215 and the left end 216 are the ends of the right side portion 212 and the left side portion 213, respectively, which are the both ends of the U-shaped dentition covering part 21.

Figure 3A:
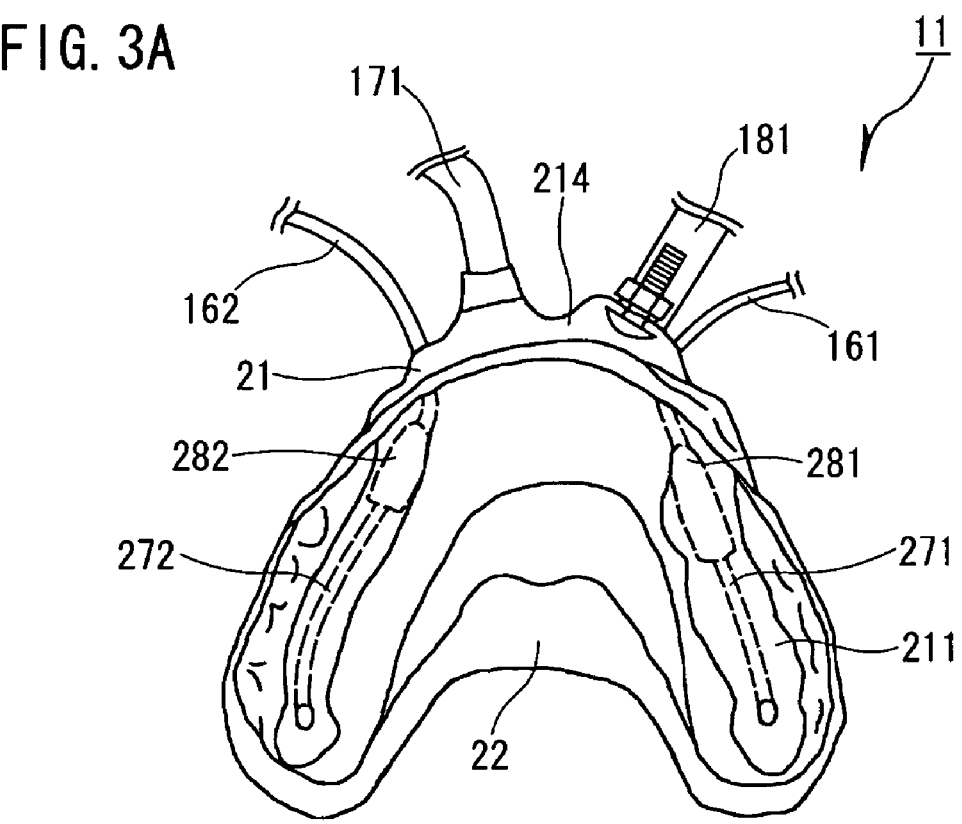
FIGS. 3A and 3B are plan views showing a mouthpiece in accordance with one embodiment of the invention.

FIG. 3A is a plan view showing the reverse side of the mouthpiece 11, and 3B showing the obverse side.

As shown in FIG. 3A, each of the drain tube 171 and the vibrating unit 18 is attached substantially perpendicularly to the front portion 214 of the dentition covering part 21. In this configuration, when a user wears the mouthpiece 11, the drain tube 171 and the vibrating unit 18 come out from the front of the oral cavity (or near the front teeth) of the user. This allows the user to brush teeth without being blocked by the tubes nor the unit.

Figure 3B:
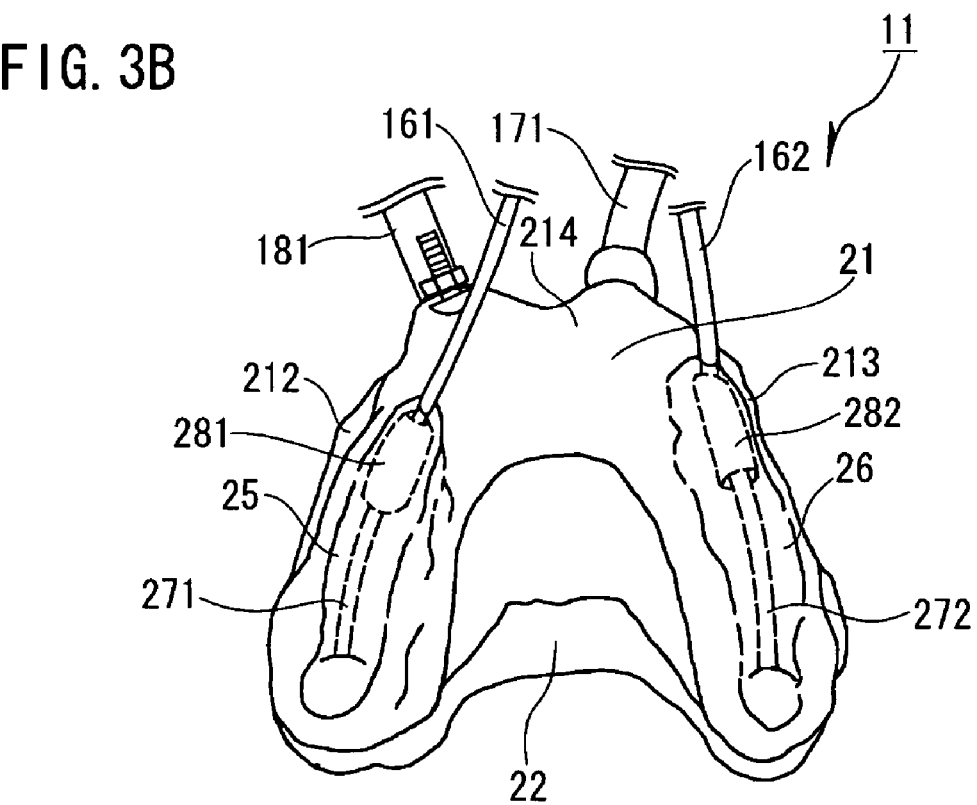

Referring now to FIG. 3B, buried tubes 271 and 272, and tube adapters 281 and 282 are embedded in the bumps 25 and 26, respectively, of the right side portion 212 and the left side portion 213. The buried tubes 271 and 272 help the drug solution 121 from the supply tubes 161 and 162 to flow into the mouthpiece 11. The tube adapters 281 and 282 are connected to the supply tubes 161 and 162, respectively, at one ends and to the buried tubes 271 and 272, respectively, at the other ends, thereby connecting the supply tubes 161, 162 to the buried tubes 271, 272.

The supply tubes 161 and 162 lie along the right side portion 212 and the left side portion 213, respectively, of the dentition covering part 21, and project from the front portion 214. Thus, when a user wears the mouthpiece 11, the supply tubes 161 and 162 come out from the front of the oral cavity (or near the front teeth) of the user. This allows the user to toothbrush without being blocked by the tubes.

Figure 4A:
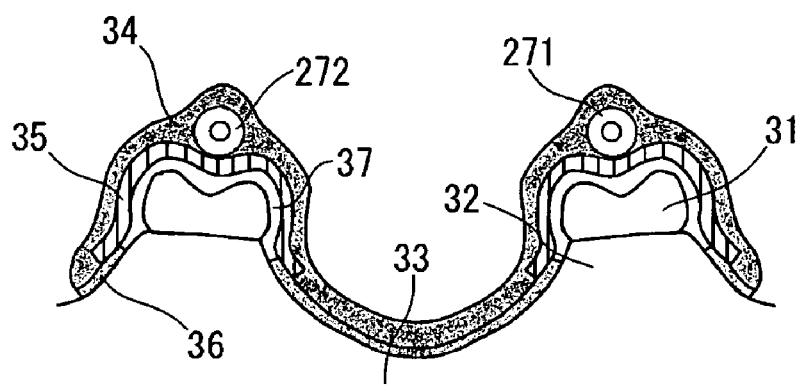
FIGS. 4A, 4B, and 4C are sectional views showing a mouthpiece in accordance with one embodiment of the invention.
Figure 4B:
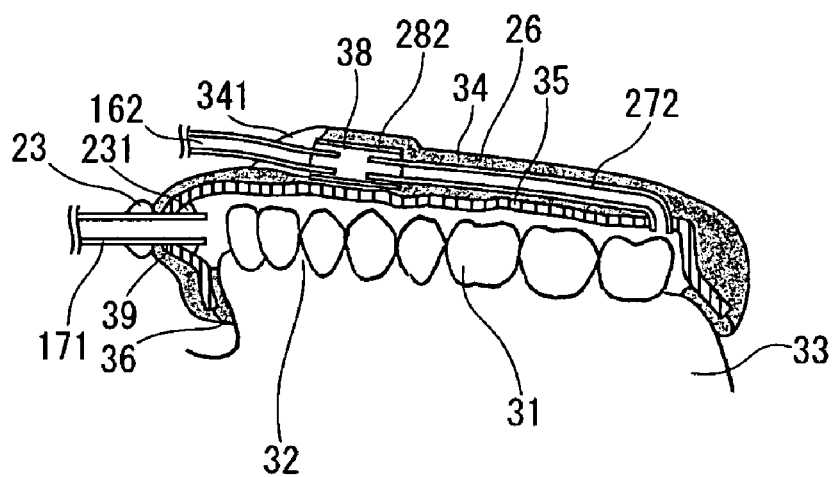
Figure 4C:
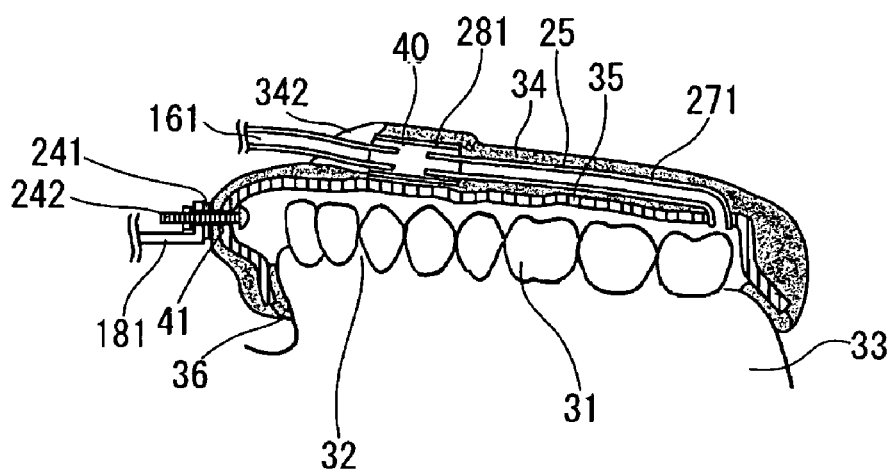

FIGS. 4A, 4B, and 4C are sectional views of the mouthpiece 11 placed in a mouth. FIG. 4A shows a cross-section along line A–A' in the right side portion 212, 4B along line B–B' in the left side portion 213, and 4C along line C–C' in the front portion 213.

As shown in FIG. 4A, the mouthpiece 11 is placed to cover dentition 31 and marginal gingiva 32 and fit over an upper jaw 33. The mouthpiece 11 comprises two layers of resins 34 and 35 above the dentition 31, while comprising three layers of resins 34, 35, and 36 above the marginal gingiva 32 and the upper jaw 33. A gap 37 having the same width as the thickness of the resin 36, is thus produced between the dentition 31 and the reverse side of the mouthpiece 11. During cleaning, the gap 37 is filled with the drug solution 121 to wash the dentition 31 and the marginal gingiva 32.

The resins 34 and 36 are flexible resins such as an ethylene-vinyl acetate copolymer resin or a polyethylene resin since a user may touch the resin 34 and the resin 36 may touch an upper jaw. The resin 35, on the other hand, is a rigid resin such as a polystyrene resin, a polycarbonate resin, or an acrylic resin since it acts as a core for supporting the mouthpiece 11 above the dentition 31.

Referring next to FIG. 4B, the tube adapter 282 placed inside the bump 26 at the left side portion 213 of the dentition covering part 21 is tube-shaped, having a bore 38 in the longitudinal direction. One end of the supply tube 162 is inserted into the bore 38 of the tube adapter 282 and is fixed at the end of the bump 26 near the front portion 214 of the mouthpiece 11, sealed with the adhesive 341 such as a self-curing resin. This end of the supply tube 162 fits into one end of the tube adapter 282 inside the bump 26. The other end of the supply tube 162 extends out of the dentition covering part 21. The buried tube 272, which fits into the other end of the tube adapter 282, penetrates through the left side portion 216 of the dentition covering part 21 to supply the drug solution 121 from the supply tube 162 inside the dental arch covering portion 21.

Further, a penetration hole 39 is provided at the front portion 214 of the mouthpiece 11. The drain tube 171 is inserted into the penetration hole 39, and fixed outside with the adhesive 23 and inside with the adhesive 231. The drain tube 171 and the supply tube 162 are thus attached in the opposite positions, front and back, of the mouthpiece 11. In this configuration, the drug solution 121 inflows from the back, passes through teeth and marginal gingiva, and then is sucked into the drain tube 171 at the front, thereby ensuring cleaning of the teeth and marginal gingiva.

Referring then to FIG. 4C, the tube adapter 281 placed inside the bump 25 at the right side portion 212 of the dentition covering part 21 is tube-shaped, having a bore 40 in the longitudinal direction. One end of the supply tube 161 is inserted into the bore 40 of the tube adapter 281 and is fixed at the end of the bump 25 near the front portion 214 of the mouthpiece 11, sealed with the adhesive 342 such as a self-curing resin. This end of the supply tube 161 fits into one end of the tube adapter 281 inside the bump 25. The other end of the supply tube 161 extends out of the dentition covering part 21. The buried tube 271, which fits into the other end of the tube adapter 281, penetrates through the right side portion 215 of the dentition covering part 21 to supply the drug solution 121 from the supply tube 161 inside the dental arch covering portion 21.

At the front portion 214 of the mouthpiece 11, there is provided a penetration hole 41 where the tip portion 181 of the vibrating unit 18 is inserted. The tip portion 181 is secured to the dentition covering part 21 with the screw 242, and further fixed at the penetration hole 41, sealed with the adhesive 241.

Now, a production process of the mouthpiece 11 is explained hereinafter with reference to FIGS. 5A, 5B, 5C, 6A, 6B, and 6C. The figures are perspective views illustrating a production process of the mouthpiece 11. Though the explanation is given on the mouthpiece 11 for upper teeth, the mouthpiece for lower teeth may be produced in the same manner.

Figure 5A:
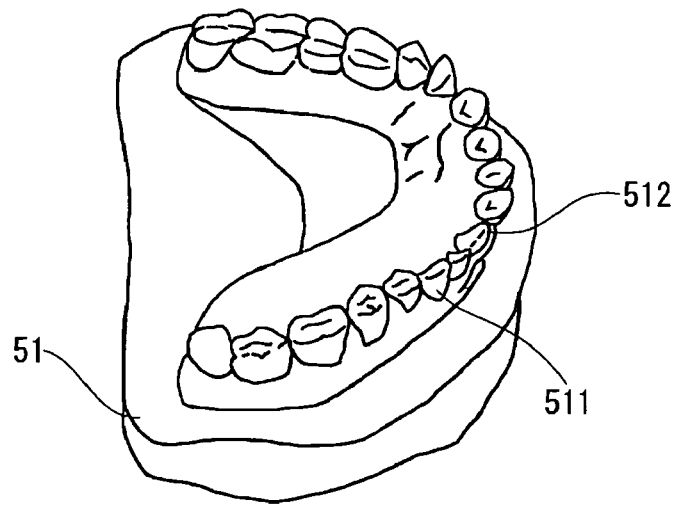
FIGS. 5A, 5B, and 5C are perspective views showing a production process of a mouthpiece in accordance with one embodiment of the invention.
Figure 5B:
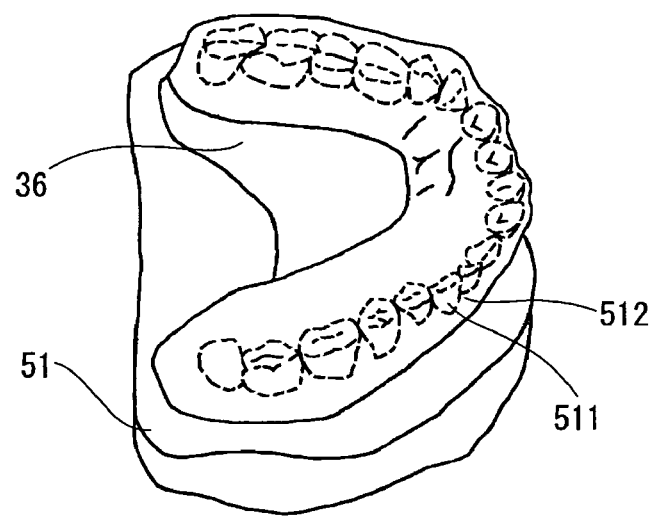

First, an impression of an upper denture of a user is taken to make a dental mold 51 of the upper denture as shown in FIG. 5A. The dental mold 51 is created for each user, thus being unique for each. Next, a dentition part 511 and a marginal gingival part 512 of the dental mold 51 are covered with a thermoplastic resin 36, and the thermoplastic resin 36 adheres to the dental mold 51 for the upper teeth as shown in FIG. 5B. The thermoplastic resin 36 is deposited to create a flow path for the drug solution 121 between the teeth with marginal gingiva and the dentition covering part 21.

The thermoplastic resin 36 may be bonded to the dental mold 51 using a dental pressure molding machine, though not illustrated. Specifically, a sub-rounded, flexible thermoplastic resin is placed to cover the dental mold 51 entirely. Next, the flexible thermoplastic resin is heated and softened. Then, air-pressure is applied to the softened resin toward the direction of the dental mold 51. The flexible thermoplastic resin 36 thereby adheres to the dental mold 51.

Figure 5C:
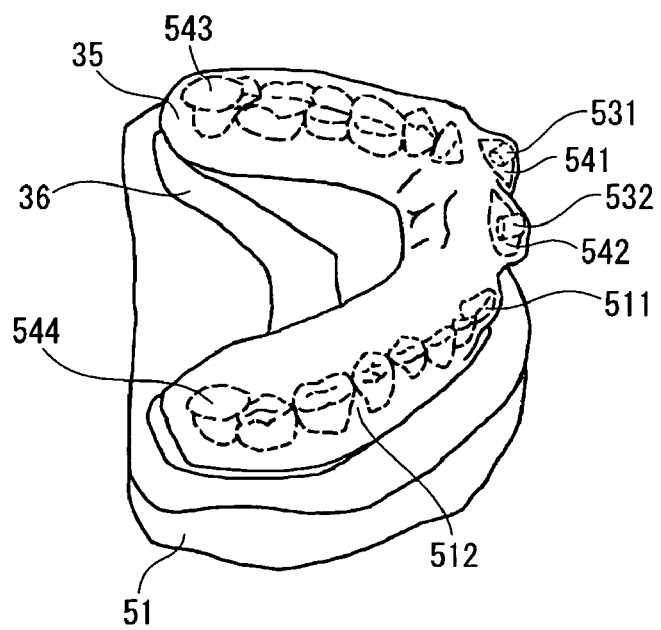

Then, two acrylic cylinders 531 and 532 are placed at the front portion 214 of the flexible thermoplastic resin 36 to form a raised portion to connect the drain tube 171 and the vibrating unit 18 as shown in FIG. 5C. The acrylic cylinders are approximately 5 mm in height, fixed near the front dentition part with adhesives 541 and 542. Further, to create spaces for easier inflow of the drug solution 121 near insertion holes 521 and 522, adhesives 543 and 544 are placed in the vicinity of the right end 215 and left end 216, respectively. The adhesives are formed to have semispherical shapes with approximately 3 mm in radius.

Further, a rigid thermoplastic resin 35 is formed on the flexible thermoplastic resin 36 adhering to the dental mold 51 using the dental pressure molding machine. The rigid thermoplastic resin 35 is then stripped off the flexible thermoplastic resin 36. The edge of the rigid thermoplastic resin 35 is cut off, leaving the part to cover the dentition part 511 and the marginal gingival part 512. After that, the resin 35 is placed back on the flexible thermoplastic resin 36. The base of the dentition covering part 21 and the upper jaw covering part 22 of the mouthpiece 11 is thereby formed.

Figure 6A:
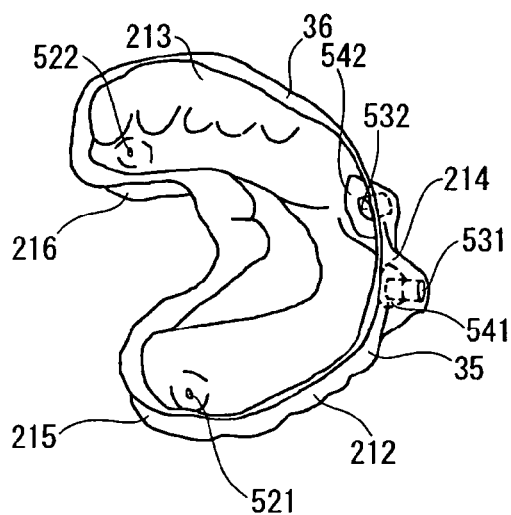
FIGS. 6A, 6B, and 6C are perspective views showing a production process of a mouthpiece in accordance with one embodiment of the invention.
Figure 6B:
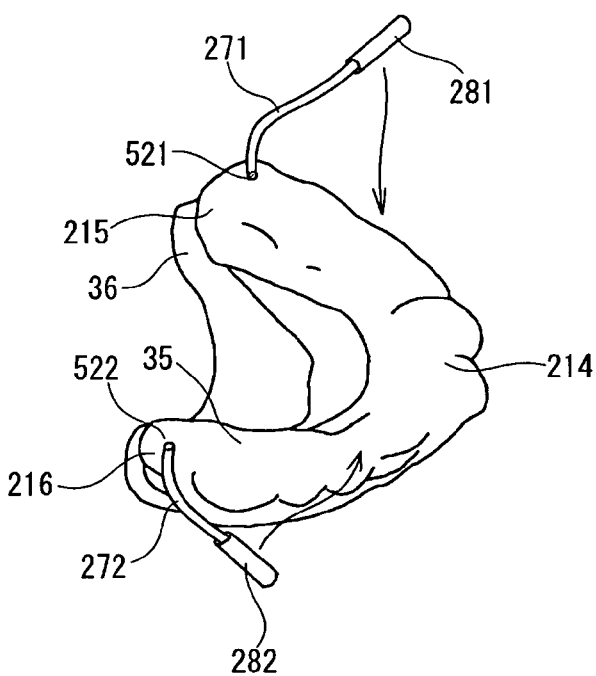

Then, the insertion holes 521 and 522 are created at the backmost of the right side portion 212 and the left side portion 213, that is, at the right end 215 and the left end 216, respectively, of the mouthpiece 11 as shown in FIG. 6A.

One ends of the buried tubes 271 and 272 are inserted into the insertion holes 521 and 522 at the right end 215 and the left end 216, respectively. The other ends are inserted into the tube adapters 281 and 282. The tube adapters 281 and 282 are attached to the rigid thermoplastic resin 35 with adhesives and so on, and the buried tubes 271 and 272 are also fixed thereby. Further, a flexible thermoplastic resin 34, which is not illustrated, is bonded thereonto using the dental pressure molding machine.

Then, the flexible thermoplastic resin 36, which is the inner layer of the mouthpiece 11, is removed only in the area that covers the dentition part 511 and a certain width of the marginal gingival part 512. This creates a gap 37 for a fluid to flow. The remaining part of the flexible thermoplastic resin 36 stays adhering to the marginal gingival part 512 of the mouthpiece 11.

The removal of the flexible thermoplastic resin 36 at the inner side of the mouthpiece 11 reveals the two cylinders 531 and 532 attached to the front portion 214 of the mouthpiece 11. The cylinders 531 and 532 are then removed, and the penetration holes 39 and 41 are created, the former for drainage of the fluid through the front portion 214 and the latter for attachment of the vibrating unit 18.

Figure 6C:
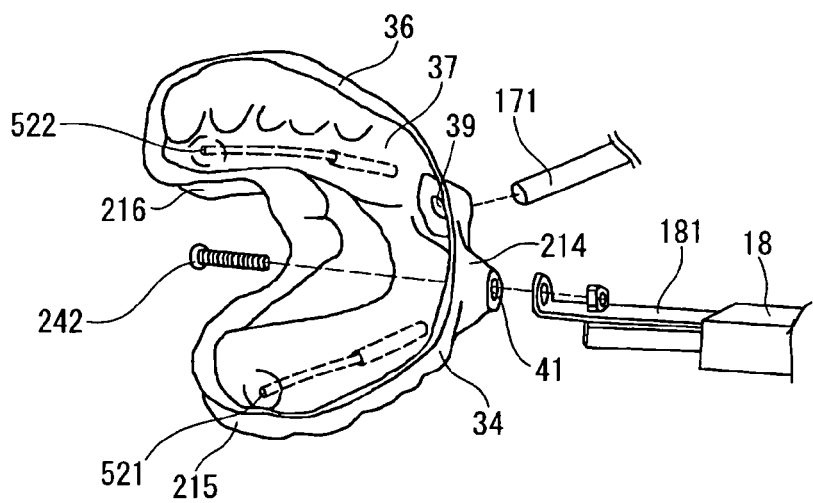

One end of the drain tube 171 is inserted and attached to the penetration hole 39 with the adhesive 23 to seal up the hole as shown in FIG. 6C. Inserted to the penetration hole 41 in the front portion 214 of the mouthpiece 11, is the tip portion 181, which is the vibrating part of the vibrating unit 18. The tip portion 181 is attached thereto with the adhesive 241 and the screw 242, sealing up the hole. Prior to this, the flexible thermoplastic resin 34 in the area around the penetration hole 41 is hollowed out by the size of the screw 242 not to be compressed by the screw 242. In this configuration, the tip portion 181 is directly attached to the resins 35 and 36, thereby effectively applying vibration to the entire mouthpiece 11.

Then, the flexible thermoplastic resin 34 is partly cut away in the vicinity of the opposite ends of the tube adapters 281 and 282 to the ends having the buried tubes 271 and 272 attached thereto. To these ends of the tube adapters 281 and 282 which are now revealed outside, the supply tubes 161 and 162 are inserted, allowing the drug solution 121 to flow inside the mouthpiece 11 through the insertion holes 521 and 522. With these tubes attached, the ends of the tube adapters 281 and 282 are fixed with adhesives. The ends of the supply tubes 161 and 162 are also sealed with the same adhesives. The buried tubes 271, 272, and the tube adapters 281, 282 are thereby embedded in the flexible thermoplastic resin 34, producing the mouthpiece 11 of a triple-layered structure.

Finally, the shape of the mouthpiece 11 is adjusted by cutting away its edge to fit in a mouth. The dentition covering part 21 and the upper jaw covering part 22 are thereby produced. The flexible thermoplastic resin 36 adhering to the marginal gingival part 512 surrounding the dentition part 511 is likely to come away from the rigid thermoplastic resin 35. To prevent this, the flexible thermoplastic resin 36 is bonded to the rigid thermoplastic resin 35 with an adhesive.

Now, a cleaning process using the dental system 10 according to this invention is explained hereinbelow. Though the following explanation is given on the mouthpiece 11 for upper teeth, a cleaning process using the mouthpiece for lower teeth may be performed in the same manner.

First, the mouthpiece 11 is placed in the oral cavity to fit on the upper teeth in a sitting or lying position. The supply tubes 161, 162, the drain tube 171, and the vibrating unit 18 come out of the mouth since they are attached to the front portion 214 of the mouthpiece 11. While the upper jaw covering part 22 of the mouthpiece 11 is in close contact with the marginal gingiva, there is a gap between the mouthpiece 11 and the teeth with a certain width of the marginal gingiva, for the drug solution 121 to flow.

Next, the drug solution 121 is poured into the supply tank 12, into which one ends of the supply tubes 161 and 162 outside of the mouth are placed. Then, the suction unit 15 is driven, and thereby suction is applied to the end of the drain tube 171 outside of the mouth through the suction tube 173 and the transfer tube 172.

Since negative pressure is provided through the suction tube 173, the inside of the mouthpiece 11 is negatively pressured; the mouthpiece 11 is thus more tightly attached onto the oral cavity. Particularly, the flexible thermoplastic resin 36 adheres to the upper teeth and the marginal gingiva of a user. The pressure inside the mouthpiece 11 thereby decreases. Since the supply tubes 161 and 162 have smaller diameters than the drain tube 171, the drug solution 121 in the supply tank 12 is sucked up through the supply tubes 161 and 162 to the inside of the mouthpiece 11. Further, the supply tubes 161 and 162 being smaller than the drain tube 171 allows preventing waste fluid in the drain tank 13 from flowing back into the mouthpiece 11.

The drug solution 121 flows through the mouthpiece 11, touching the teeth and marginal gingiva, and is drained out through the drain tube 171. The debris on the teeth and marginal gingiva is thereby washed out. If the drug solution 121 is an antiseptic solution, the teeth and marginal gingiva can be sterilized. This system requires only such a small amount of the drug solution 121 that flows through the gap 37 in the mouthpiece 11, thus reducing the cost of the drug solution 121. Further, since the drug solution 121 flows through the mouthpiece 11, not flowing into a throat, the user can perform teeth cleaning without the risk of side effects of the drug solution.

Moreover, no drug solution leaks since the mouthpiece 11, especially the flexible thermoplastic resin 34, is in close contact with the upper jaw and the marginal gingiva of the user. The drug solution 121 thus does not touch the tongue and other mucosa in the oral cavity, allowing the user comfortable cleaning without feeling an unpleasant flavor.

While the drug solution 121 is flowing, the vibrating unit 18 attached to the mouthpiece 11 is set to vibrate. The mouthpiece 11 thereby vibrates, which applies vibration to the teeth and marginal gingiva through the drug solution 121 inside the mouthpiece 11. This can easily wash away the debris on the teeth and marginal gingiva. This also allows gingival massage with the vibration of the mouthpiece 11 applied to the marginal gingiva.

As described above, the mouthpiece 11 of the dental system 10 has a unique shape for each user. When in use for cleaning and disinfecting, the mouthpiece 11 covers the teeth and marginal gingiva of the user and adheres to the marginal gingiva. The drug solution 121 thereby does not leak out of the mouthpiece 11. This prevents the drug solution 121 from touching the tongue of the user, allowing the user to clean the teeth and marginal gingiva without feeling an unpleasant flavor.

Further, the debris taken out by the drug solution 121 is sucked up by the suction unit 15, which ensures removal of the debris from the oral cavity. This achieves effective cleaning and disinfecting while preventing misswallowing, eliminating the risk of side effects of the drug solution 121. Furthermore, since the mouthpiece 11 is made of flexible material, it covers teeth, marginal gingiva, and upper jaw (or under jaw for the mouthpiece for under teeth) thinly and smoothly. This helps to reduce uncomfortable feeling when a tongue touches the mouthpiece 11, not stimulating the vomiting reflex.

In the dental system 10, the mouthpiece 11 vibrates by the vibrating unit 18, which applies vibration to the teeth and marginal gingiva, thereby allowing complete cleaning. In addition to teeth and gingiva cleaning effect, use of the vibrating unit 18 has gingival massaging effect since vibration is applied to the marginal gingiva adhering to the mouthpiece 11. Further, use of the vibrating unit 18 only requires holding it with one hand at a certain position, not causing hand fatigue. The dental system 10 is thus user-friendly for those who are aged or have handicap with hand, offering them proper mouth cleaning.

The dental system 10 is particularly effective in cleaning teeth under orthodontic treatment. During the orthodontic treatment, an orthodontic brace called bracket is attached directly to the tooth surface. Surface deposits such as plaque and calculus build up around the bracket or on wires between the brackets; however, brushing is unable to remove the deposits because of wires. Use of the dental system 10, which cleans teeth and marginal gingiva with a fluid such as a cleaning solution flowing through the mouthpiece 11, ensures removal of the surface deposits since the fluid can flow into difficult areas such as around brackets and under wires. Further, it achieves a significant effect on oral cavity cleaning or treatment of gingivitis or alveolar pyorrhea for those who are aged or have handicap with hand.

The dental system 10 is also useful for patients who have had bone grafting in cleft lip and palate and so on. The bone grafting surgery saws the nasal cavity side of a mucoperiosteal flap shut to close the nasal cavity and injects bone and marrow from the patient's hip thereinto. The surgery then saws the palate side of a mucoperiosteal flap shut to suture a wound. After three months in this state, the harvested graft works as a jaw bone. It does not, however, survives if bacterial infection occurs or the grafted part is compressed in this period. Thus, to prevent compression of the palate, patients generally wear a denture, which is also called a plate or a guard, until the graft starts functioning.

Using the mouthpiece 11 of the dental system 10 instead of the plate allows keeping the grafted part clean. It also allows delivering a biochemical substance called bone growth factor through the mucosa.

Further, the dental system 10 is effective in bone grafting for aged patients. Those who lost teeth due to dental caries or alveolar pyorrhea generally have a denture made by taking an impression. However, the alveolar bone under the part where teeth are lost is likely to be eroded flat with age, making it difficult to hold the denture. For those who have decreased alveolar bone, there are techniques that increase the alveolar bone by grafting a bone from a hip. Among those is a technique that adds a gel solution of a biochemical substance called bone growth factor to an alveolar bone, thereby building the alveolar bone. In this technique, however, a high pressure is applied to the surface mucosa over the alveolar bone, causing the injected gel solution to be reduced accordingly.

Use of the dental system 10 can reduce the pressure that interferes with the treatment since the marginal gingiva inside the mouthpiece 11 is negatively pressured, which applies pressure to the surface mucosa over the alveolar bone in the opposite direction from the alveolar bone compressing pressure. Further, using the dental system 10 can eliminate bacteria in an oral cavity by the flow of an antibacterial agent, enhancing the treatment progress. Furthermore, vibration from the vibration unit 18 stimulates the proliferation of bone growth cells.

In a case of brushing teeth in a spacecraft and the like under weightless conditions, fine droplets are spluttered out of the mouth, contaminating the spacecraft. To prevent the droplets from spluttering out of the mouth, crew members cannot brush their teeth satisfactory; besides, they swallow waste fluid or spit it out into a towel. Use of the dental system 10 allows them proper toothbrushing, with the suction unit 15 ensuring suction of waste fluid into the drain tank 13. It avoids contamination of the spacecraft in a weightless state, preventing equipment breakdown in the spacecraft.

Figure 7:
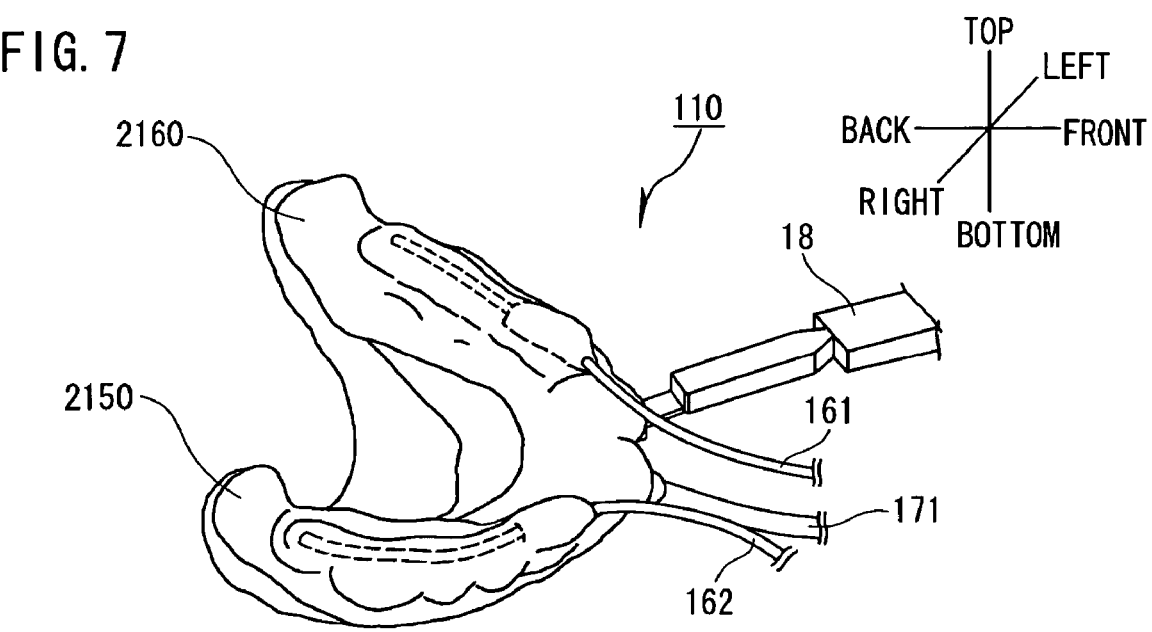
FIG. 7 is a perspective view showing a mouthpiece in accordance with one embodiment of the invention.

Referring finally to FIG. 7, a mouthpiece 110 for lower teeth is shown. FIG. 7 is a perspective view illustrating an obverse side of the mouthpiece 110.

As shown in FIG. 7, the mouthpiece 110 has a right side end 2150 and a left side end 2160 that are warped toward an upper jaw to follow the shape of the retromolar triangle in the lower jaw. This is different from the mouthpiece 11 for upper teeth. The mouthpiece 110 thereby fits over the retromolar triangle in the back of the back teeth of a user. This confines the drug solution 121 in the mouthpiece 110, ensuring cleaning of the lower teeth of the user.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A dental system for cleaning a user's teeth and marginal gingiva with a drug solution, comprising:
   a mouthpiece made for a user, the mouthpiece having a shape unique to the user, the shape being substantially the same shape as the teeth and the marginal gingiva of the user, the mouthpiece being a laminate structure including a first resin layer portion and a second resin layer portion adhered to the first resin layer portion, the first resin portion conforming to and sealing with the user's marginal gingiva and jaw, the second resin portion conforming with the user's teeth and marginal gingiva the second resin portion providing a gap between the mouthpiece and the user's teeth and marginal gingiva, a width of the gap corresponding to a thickness of the first resin layer portion;
   a supply unit, connected to the mouthpiece, that supplies the drug solution to the mouthpiece;
   a drain unit, connected to the mouthpiece, that collects the drug solution supplied to the mouthpiece by the supply unit; and
   a suction unit, connected to the drain unit, that introduces the drug solution from the supply unit into the mouthpiece by applying suction to the drain unit, the suction unit providing a negative pressure within the gap and forming a stream of the drug solution flowing through the gap that clean the user's teeth and marginal gingiva.

2. A dental system according to claim 1, wherein the supply unit comprises a tube branching into at least two tubes, one tube for supplying the drug solution through a vicinity of a right back tooth of the user wearing the mouthpiece, another tube for supplying the drug solution through a vicinity of a left back tooth of the user.

3. A dental system according to claim 1, wherein the first resin layer portion is a flexible resin, and the second resin layer portion is a rigid resin.

4. A dental system according to claim 1, wherein the supply unit is connected to a back tooth portion of the mouthpiece to supply the drug solution through the back tooth portion, and the drain unit is connected to a front tooth portion of the mouthpiece to supply the drug solution through the front tooth portion.

5. A dental system according to claim 4, wherein the supply unit supplies the drug solution via a route from the front tooth portion, through an inside of the mouthpiece, to the back tooth portion.

6. A dental system according to claim 1, further comprising a vibrating unit connected to the mouthpiece, for applying vibration to the mouthpiece.

7. A dental system according to claim 6, wherein the vibrating unit is connected to a front tooth portion of the mouthpiece to apply vibration to the mouthpiece through the front tooth portion.

8. A method of producing a dental system for cleaning a user's teeth and marginal gingiva with a drug solution, comprising steps of:
   making a dental mold having substantially the same shape as the teeth and the marginal gingiva of the user;
   attaching a first resin onto the dental mold;
   attaching a second resin onto the first resin;
   stripping the first resin and the second resin out of the dental mold, and creating a first hole and a second hole penetrating the first resin and the second resin;
   stripping a part of the first resin placed on a tooth portion and a vicinity of the tooth portion the dental mold out of the second resin;

connecting a supply unit to the first hole, for supplying the drug solution;

connecting a drain unit to the second hole, for collecting the drug solution; and connecting a suction unit to the drain unit, for sucking up the drug solution from the supply unit through the drain unit.

9. A method of producing a dental system according to claim 8, further comprising steps of:

creating a third hole penetrating the first resin and the second resin; and connecting a vibrating unit to the third hole, for applying vibration.

10. A method of producing a dental system according to claim 8, further comprising a step of attaching a third resin onto a part of the second resin where the supply unit is placed, to cover the part with the third resin.

11. A method of producing a dental system according to claim 10, wherein the step of stripping the first resin out of the second resin comes after the step of attaching the third resin.

12. A dental system according to claim 1, wherein the width of the gap is uniform.

13. A dental system according to claim 1, wherein the width of the gap is equal to the thickness of the first resin layer portion.

14. A dental system according to claim 1, wherein the suction unit provides a negative pressure in the gap that tightens a seal between the first resin layer portion and the user's marginal gingiva.

* * * * *